United States Patent [19]
Greenshields et al.

[11] Patent Number: 5,530,112
[45] Date of Patent: Jun. 25, 1996

[54] GEL PRODUCTION FROM PLANT MATTER

[75] Inventors: Roderick Greenshields, Swansea; Artis L. Rees, Pontardawe, both of Wales

[73] Assignee: GB R&D, C Limited, Swansea, United Kingdom

[21] Appl. No.: 240,651

[22] PCT Filed: Nov. 16, 1992

[86] PCT No.: PCT/GB92/02125

§ 371 Date: May 13, 1994

§ 102(e) Date: May 13, 1994

[87] PCT Pub. No.: WO93/10158

PCT Pub. Date: May 27, 1993

[30] Foreign Application Priority Data

| Nov. 16, 1991 | [GB] | United Kingdom | 9124427 |
| Mar. 12, 1992 | [GB] | United Kingdom | 9205406 |
| Apr. 27, 1992 | [GB] | United Kingdom | 9209094 |
| Jul. 7, 1992 | [GB] | United Kingdom | 9214392 |

[51] Int. Cl.$^6$ .............. C08B 37/14; C08L 5/14; A61L 25/00; A61L 27/00
[52] U.S. Cl. .............. 536/123.1; 536/127; 536/128; 424/488
[58] Field of Search .............. 536/123.1, 127, 536/128; 424/484, 485, 488

[56] References Cited

U.S. PATENT DOCUMENTS

| 4,262,024 | 4/1981 | Mathason | 426/231 |
| 4,831,127 | 5/1989 | Weibel | 536/56 |
| 5,099,009 | 3/1992 | Thibault et al. | 536/2 |
| 5,174,998 | 12/1992 | Ijitsu et al. | 424/410 |

FOREIGN PATENT DOCUMENTS 2545101 4/1983 France.

WO91/06323 5/1991 WIPO.

OTHER PUBLICATIONS

Geissmann et al., "On the Composition of the Water Soluble Wheat Flour Pentosans and their Oxidative Gelation", *Lebensm.–Wiss. U. Technol*, 6, pp. 59–62 (1973).

Michniewicz et al., "Water–Insoluble Pentosans of Wheat: Composition and Some Physical Properties", *Cereal Chemistry*, 67, pp. 434–439 (1990).

Izydorczyk et al., "Comparison of the Structure and Composition of Water–Soluble Pentosans from Different What Varieties", *Cereal Chemistry*, 68, pp. 139–144 (1991).

Geissmann et al., "Vernetzung von Phenolcarbonsäureestern von Polysaccariden Durch Oxydative Phenolische Kupplung", *Helvetica Chimica Acta*, 54, pp. 1108–1112 (1971).

Neukon et al "Oxidative Gelation of Wheat Flour Pentosans: A New Way of Cross–Linking Polymers" Cereal Foods World, Jul. 1978, pp. 374–376.

*Primary Examiner*—Nathan M. Nutter
*Attorney, Agent, or Firm*—Schwegman, Lundberg, Woessner & Kluth

[57] ABSTRACT

A method of producing a gel material and which comprises firstly providing an aqueous soluble hemicellulosic starting medium which is free of glucans and obtainable from testaceous plant material. The starting medium is then extracted with a non-acidic reagent and reacted with an oxidizing system comprising at least one peroxide, together with at least one oxygenase (such as a peroxidase).

A gel material which is obtainable from a hemicellulosic starting medium, and which is substantially free of glucans and pectins. The gel material comprises a polysaccharide network for a matrix of polysaccharide chain segments and a multiplicity of cross-linking ferulate bridges. The ferulate bridges are located at regular intervals along the cross-linked segments.

31 Claims, 6 Drawing Sheets

GEL PRODUCTION FROM PLANT MATTER

The present invention is concerned with the production of gels from plant matter and the resulting gels.

Large numbers of plant sources contain hemicelluloses, which are composed of various arrangements of pentoses (such as xylose and arabinose), hexoses (such as mannose, glucose and galactose) and/or uronic acids (such as glucuronic and galacturonic acid). Examples of hemicellulosic materials include xylans (such as arabinoxylan), mannans and galactans, which may be substituted by phenolic acid residues such as ferulic acid (4-hydroxy-3-methoxycinnamic acid), coumaric acid (p-hydroxycinnamic acid) or vanillic acid (4-hydroxy-3-methoxyl benzoic acid). Such materials occur naturally in cereals such as maize, barley (including malted barley), wheat, oats and rice; pulses, such as soya; legumes and fruit.

French patent specification 2545101 is concerned with modification of sugar beet pectins by reacting an oxidising system comprising an enzyme (such as peroxidase) and an oxidising agent (such as hydrogen peroxide) with pectins which have been isolated from sugar beet. The isolation of pectin comprises subjecting the sugar beet to acidic extraction and heat treatment.

According to the present invention, there is provided a method of producing a gel material, which method comprises:

(a) providing an aqueous soluble hemicellulosic starting medium which is substantially free of glucans and is obtainable from testaceous plant material;

(b) extracting said starting medium with a non-acidic aqueous reagent; and (c) reacting the extracted material with an oxidising system comprising at least one peroxide, together with at least one oxygenase (such as a peroxidase).

The soluble hemicellulosic starting medium is typically prepared from waste testaceous plant material containing a significant quantity (such as at least about 10%, such as about 20%) of arabinoxylan or glucuronoarabinoxylan, which is present in nature primarily in the cell wall regions. Examples of preferred such sources include waste materials which are rich in cell walls, such as cereal husk or bran, or legumes (pulses). Typical cereal husk or bran includes maize, barley, wheat, rice or oats, or malt or malt culms (dried germinated barley rootlets).

In a preferred embodiment, the hemicellulosic starting medium is in a substantially ground form having a particle size of not more than about 100 microns. The plant material is therefore typically ground, either in dry or wet form (such as milling or wet grinding known as maceration) to the required particle size. The ground material is typically air classified or sieved to remove starch. The method may comprise starch removal by suitable enzyme treatment, for example, with diatase (alpha and/or beta-amylase).

The glucans are preferably removed from the plant material by enzyme digestion with carbohydrase enzymes such as glucanase.

The insoluble enzyme treated material may then be dried (in air) before further processing. The plant material may have been pre-treated so as to remove the glucans prior to application of the present method, but it is preferred that the method according to the invention involves enzyme treatment so as to remove glucans following the above described grinding of the plant material.

Suitable glucanases for use according to the invention are commercially available under the trade marks Viscozyme, Biofeed and Biofeed Plus which typically also have hemicellulase, cellulase, arabinase and xylanase activity. Viscozyme is currently preferred.

The non-acidic extraction preferably comprises treatment with hot water or weak alkali typically of less than 0.5% by weight of the aqueous reagent. Preferred alkalies are NaOH and KOH. The alkali is preferably used in an amount of 0.1 to 10% (typically 0.5 to 2.5%) by weight of the aqueous reagent, for times of from 20 minutes to 5 hours (typically about 2 hours) Alternatively, gel may be produced from wheat bran and barley dust or culms by using hot water in place of alkali.

The alkaline extraction may be at a temperature of from 30° to 100° C. and is typically at a temperature of 60° to 90° C. generally for 10 minutes to 5 hours. For strong gels, temperatures of 60° to 75° C. are preferably used for 0.5 to 1.5 hours; for weaker gels temperatures of 6020 to 85° C. are preferably used for 2 to 5 hours. Hot water extraction is carried out at temperatures of 50° to 80° C. (typically 60° to 70° C.) for 0.5 to 2 hours (typically 1 to 1.5 hours). The extraction is generally effected with gentle stirring. The resulting extracted material generally comprises insoluble cellulose and soluble hemicelluloses; the cellulose is typically removed by centrifugation, either with or without acidification.

It is advantageous to avoid extreme conditions (such as sustained contact of the hemicellulosic medium with sodium hydroxide or temperatures above the above-described preferred range) during alkaline extraction in order to optimise the gelling characteristics of gel material produced by a method according to the present invention.

Alkaline extraction will produce an extracted material substantially free of pectins as the latter are labile in alkaline conditions and are extractable by acidic reagents as described in FR 2545101.

Following alkaline extraction the hemicellulosic material, which is rich in arabinoxylans and is substituted by phenolic acids, is preferably neutralised (for example, using hydrochloric, sulphuric, acetic or citric acid, of which citric acid is preferred). Neutralisation is advantageous in that it helps to preclude rapid hydrolysis of ferulic acid residues present in the extracted material; such hydrolysis would damage the gelling properties of the material. The solids can be removed from the neutralised extract by filtration or centrifugation which results in improved gel properties.

Purification of the hemicellulosic material may then be carried out be precipitation with an alcohol such as methanol or ethanol (or industrial methylated spirit), or iso-propanol (propan-2-ol). Such alcohols may be added in amounts of from 1.5 to 3.5 volumes according to the fraction desired by molecular weight. The hemicellulosic material may alternatively be purified by passage through an activated carbon column and subsequently concentrated by precipitation with ammonium sulphate at 70–80% saturation or any of the above alcohols used for precipitation. Alternatively the concentration of the eluate may involve drying (such spray or vacuum rotary drying) and redissolving of the eluate.

The hemicellulosic material may be further purified by ion-exchange treatment, preferably with a cation exchange resin to remove cationic impurities.

Differential precipitation or selection by molecular weight cut-off (e.g. diafiltration or cross-flow filtration) at this stage can provide fractions of the polysaccharide which vary in molecular weight and exhibit different rheological properties and consequently viscoelastic properties of the gels they produce. For example precipitation with ammonium sulphate at saturations of between 60 and 80% yields fractions differing in molecular weight; similarly addition of ethanol of 1.7 to 3 volumes yields the same range of fractions.

After separation by filtration or centrifugation, and redissolving of the precipitate in water, a second precipitation may be carried out by addition of 2 to 4 volumes of alcohol. The fraction obtained may be filtered (and dried on the filter using ether) or redissolved in water and lyophilised.

The salt content may be lowered if wished (for example, if the final gel is to be used in foodstuffs), typically by dialysis or tangential flow ultrafiltration. The de-salted material may be separated on an anion exchange resin such as Purolite A500 to produce fractions differing in charge (dependent on uronic acid content). Selection of fractions at this stage can further control the rheological/viscoelastic properties of the final product. The resulting material may be dried (for example, by spray drying, freeze drying, vacuum rotary drying or drying on a filter using diethyl ether) at this stage; the resulting dried material may be rehydrated prior to treatment with an oxidising system as described below.

The rehydrated material (or, if relevant, the non-dried material) is then treated with a peroxide (such as $H_2O_2$) and a peroxidase (such as horseradish peroxidase). By varying the hydrogen peroxide concentration, and hence the number of free ferulic acid groups that become di-ferulic cross links, the extent of cross-linking within the resulting gel can be controlled. For example, a 0.5% solution of the hemicellulosic starting medium may produce gels with "hardness" varying from 0.008 kg to 0.058 kg by adjusting the concentration of hydrogen peroxide in the enzymic reaction. The term "hardness" is a measure of the viscoelastic properties of the gel.

The gel properties may be further modified by the conditions used in peroxidase treatment. The treatment with a peroxidase (with a small amount of the peroxide) can result in a weak to strong clear gel at concentrations of 0.05 to 10% (preferably 0.5 to 2.5%). The balance is generally water. Polyvalent metal cations (such as $Ca^{2+}$, $Cu^{2+}$, $Zn^{2+}$, $Fe^{3+}$ or $Al^{3+}$) added prior to peroxide/peroxidase treatment will modify the gels, for example such that they can subsequently break into sols.

In any case, the resulting gel, which is constituted of cross-linked fibrous material comprising a phenolic acid substituted polysaccharide network, typically rich in arabinoxylans, is highly thermostable and may be autoclaved. (For example, the gel may withstand 15 psi at 122° C. for 15 minutes). The purified gels in particular can be made with reproducible viscoelastic and rheological properties.

Further control over the viscoelastic properties (such as brittleness) may be exercised by addition of sugar, salts or alcohols, or by treatment with carbohydrase enzymes.

The peroxidase is typically used in an amount of 1 to 100 micrograms per gram of substrate; the peroxide is typically used in an amount of the order of one tenth of the amount of peroxidase.

According to a first aspect of the present invention, there is provided a gel material obtainable from a hemicellulosic starting medium, said gel material being substantially free of glucans and pectins and comprising a polysaccharide network which comprises:

(i) a matrix of polysaccharide chain segments; and (ii) a multiplicity of cross-linking ferulate bridges disposed at bonding locations at substantially regular intervals along cross-linked segments.

The gel material according to the first aspect of the present invention is characterised by infra-red absorbance both in the wavelength range of 1550–1600 $cm^{-1}$ and in the wavelength range of 1100–1160 $cm^{-1}$.

According to a second aspect of the present invention, there is provided a gel material obtainable from a hemicellulosic starting medium, said material comprising a polysaccharide matrix having a substantially regular array of cross-linking bridges and being characterised by infra-red absorbance both in the wavelength range of 1550–1600 $cm^{-1}$ and in the wavelength range of 1100–1160 $cm^{-1}$.

The gel material according to the second aspect of the present invention is preferably substantially free of glucans and pectins. The absence of these relatively large sugar units facilitates the formation of cross-linking bridges within the polysaccharide matrix.

The polysaccharide matrix preferably comprises a multiplicity of polysaccharide chain segments joined by means of the cross-linking bridges. The regular array of cross-linking bridges typically consists essentially of ferulate bridges disposed at bonding locations at substantially regular intervals along the chain segments of the polysaccharide matrix. The ferulate moieties are responsible for the characteristic infra-red absorbance both in the wavelength range of 1550–1600 $cm^{-1}$ and in the wavelength range of 1100–1160 $cm^{-1}$ exhibited by the gel material.

The frequency of ferulate bridges within the polysaccharide network influences the properties of the resulting gel. As described above, the extent of ferulate cross-linking can be substantially controlled by selected reaction conditions during treatment with the peroxide and oxygenase, wherein ferulic acid residues are oxidatively coupled to form the di-ferulate cross-links.

A gel material provided with a substantially regular arrangement of ferulate bridges as described above closely approximates an "ideal gel system". The term "ideal gel system" as used herein denotes a gel of substantially ordered macromolecular structure, the production of which is desirable due to the substantially predictable properties of the resultant gel.

A gel according to the present invention is preferably obtained from a hemicellulosic starting medium according to a method substantially as hereinbefore described. The present invention therefore allows the production of an ideal gel system from a naturally occurring biological material. The above definition of a gel according to the present invention also encompasses a gel material obtained by chemical synthesis techniques.

It is preferred that the polysaccharide network comprises a plurality of discrete polysaccharide chains linked by means of the ferulate bridges. The polysaccharide chain segments are preferably rich in arabinoxylan or glucuronoarabinoxylan moieties. Typically, the molecular integrity of the arabinoxylan or glucuronoarabinoxylan moieties is substantially disrupted as a result of enzyme treatment of the hemicellulosic starting medium. As hereinbefore described, the enzyme treatment typically involves treatment by suitable glucanases, such as glucanases commercially available under the trade marks Viscozyme, Biofeed and Biofeed Plus.

The gel material may further comprise an aqueous liquid, such as water, which is preferably present in an amount of 98–99.9% by weight. There may further be present in the gel material metal cations as hereinbefore described.

The molecular weight of the gel material according to the present invention is typically in the range of 80 to 600 kdaltons (more generally 90 to 500 kdaltons).

There is further provided by the present invention a gel material obtained by a method substantially as hereinbefore described.

Viscous solutions rather than gels can be produced by either further limitation of the peroxide concentration or by using a solution having a hemicellulosic concentration below the critical gel-forming concentration of about 0.05%.

For example, solutions of viscosity varying between 100 and 500 cP may be produced from a 0.1% hemicellulosic concentration by limiting the peroxide concentration to levels below those which form gels.

An extract produced substantially as hereinbefore described may co-gel with other hemicellulosic-derived materials in such a way that the two gelling agents are synergistic. For example, extract material derived from maize in the method according to the invention may be blended with extract material derived from other cereals (such as wheat, malt or barley) in the method according to the invention, in proportions in which neither would form a firm gel along, but a firm gel is formed with the two materials. For example, a firm gel can be obtained with 0.7 to 3% of material derived from maize and about 2% of material derived from wheat (all the above proportions being on a solids basis).

The gel material according to the invention may have a wide variety of uses, of which the following are exemplary:
1. In medicinal compositions for example as a topical formulation or wound dressing (such as for treatment of burns) or debriding agent, as a carrier for iron or zinc, as a lubricant, or a thickener for parenteral compositions, or as an encapsulating agent, or as a slow release vehicle for drug delivery (either for oral, parenteral or anal delivery), or for use for implants and prosthesis purposes for orthopaedic purposes (such as pressure-relief gels), for ocular purposes or suppository uses. A particularly preferred medicinal application of the gel is for use as a wound dressing, and there is further provided by the present invention a wound dressing having a surface contact region comprising a gel as hereinbefore described. Advantageously, the wound dressing consists essentially of a gel material substantially as hereinbefore described.
2. In foodstuffs or animal feeds, for example, as a cold setting gel for use as a stabiliser for ice cream or the like, as a suspending agent for particles such as coconut, as a glazing agent for meat or the like, as a setting agent for jams, or a thickening agent for gravies, purees, sweets, soups or the like, as a soluble fibre, as a food lubricant, as a viscosity agent for flavours, as a canning gel, functional food or fish bait.
3. In the oil industry, for example, for sealing strata above oil deposits, as an oil drilling sealing agent, as an additive to drilling muds or the like, and for recovery of oil from oil-bearing strata.
4. In the microbiological industry, for example as a gelling agent, a spore biocontainer or a culture biocontainer.
5. In the agricultural industry, as a slow release pesticide biocontainer, a plant culture medium, an anti-drying agent, a silage pit sealing material, or the like.

Gels obtained according to the invention may be prepared such that they eventually break down to the sol form.

The present invention is further illustrated by reference to the following Examples and accompanying drawings which do not limit the scope of the invention in any way.

EXAMPLE 1

Production of a Firm Gel from Corn (*Zea mays*)
1. Grinding
Corn bran was subjected to grinding which involved initial wet milling followed by dry milling to an average particle size in the range of 80–300 microns.
2. Enzyme Treatment
0.01% w/w of a cytase enzyme at 45° C. for 2 to 24 hours depending on a raw material type and textures (e.g. for milled corn bran a period of about 6 hours).
3. Alkali Extraction
A 10% (w/v) suspension of the milled corn bran in 1% w/v potassium hydroxide (aqueous) was prepared and gently stirred at 65°–80° C. for 2–3 hours.
4. Separation
The insoluble material, consisting mainly of cellulose, was removed by centrifugation at 2500 rpm.
5. Neutralisation/Dialysis
The supernatant was carefully decanted, neutralised with hydrochloric acid (or citric acid) and dialysed against running tap water for 2 days.
6. Gelling
The concentration of the dialysed extract was adjusted to 3% w/v with deionised water. 100 ml of this solution was taken and 1 ml of 100 micrograms/ml horseradish peroxidase mixed in thoroughly. When distributed, 0.5 ml of hydrogen peroxide at 40 micrograms $H_2O_2$/ml was added and mixed in; the mixture was then left to set at ambient temperature (5–15 min) or at a higher temperature (1–2 min at 40° C.).

An Instron Texture Profile Analyser was used to measure the hardness, brittleness and elasticity of the following:—a gel produced by the above example, gelatin and a pectin gel cross-linked with diferulic acid which was prepared according to the teaching of French patent specification 2545101.

Figure 1:
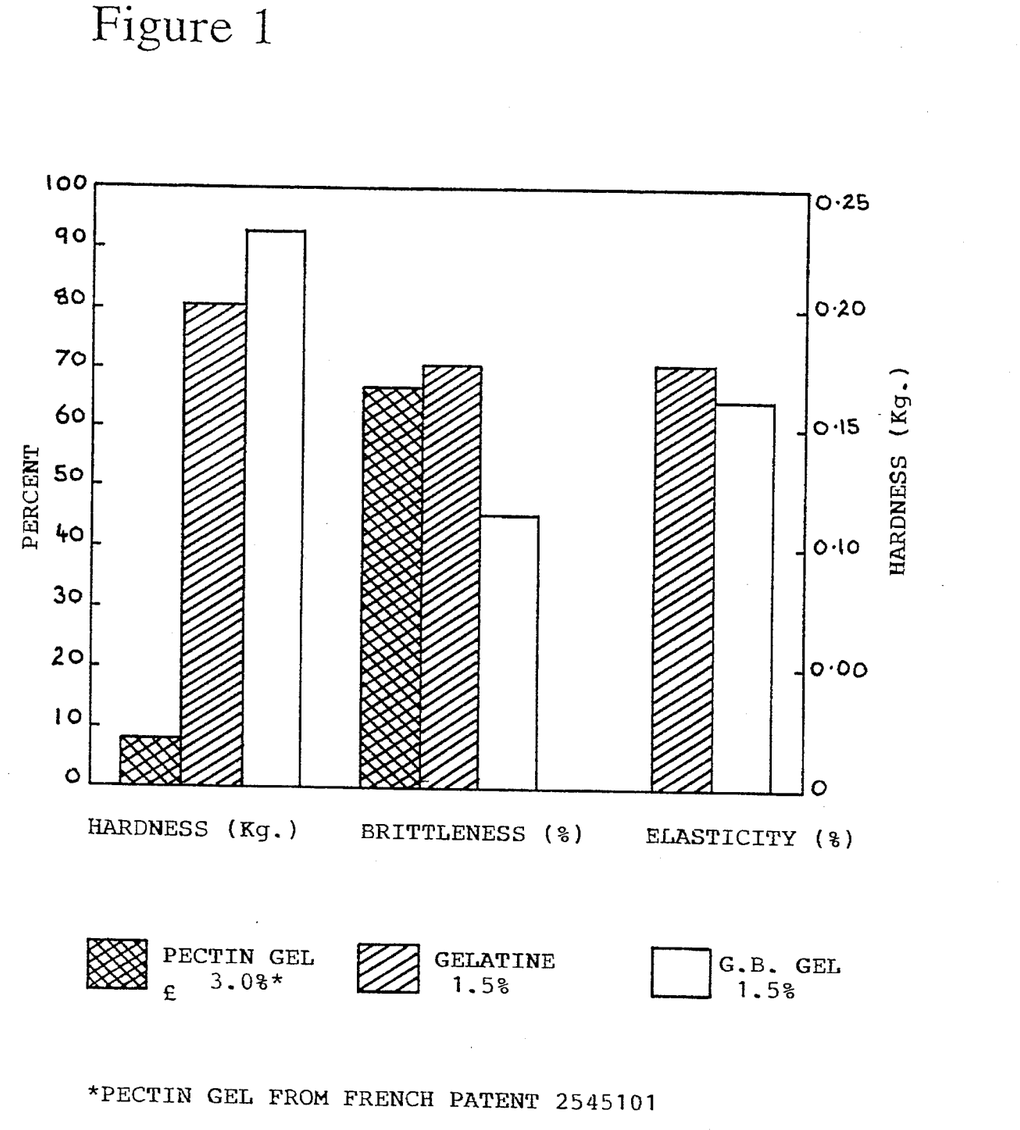
FIG. 1 is a graphic comparison of the hardness, elasticity and brittleness properties of a gel according to the present invention (identified as G. B. Gel), a pectin gel and gelatin.

As can be seen from FIG. 1, the gel according to the present invention had superior hardness compared to gelatin and the pectin gel, similar elasticity to gelatin and was less brittle than either of the other two gels.

Figure 2:
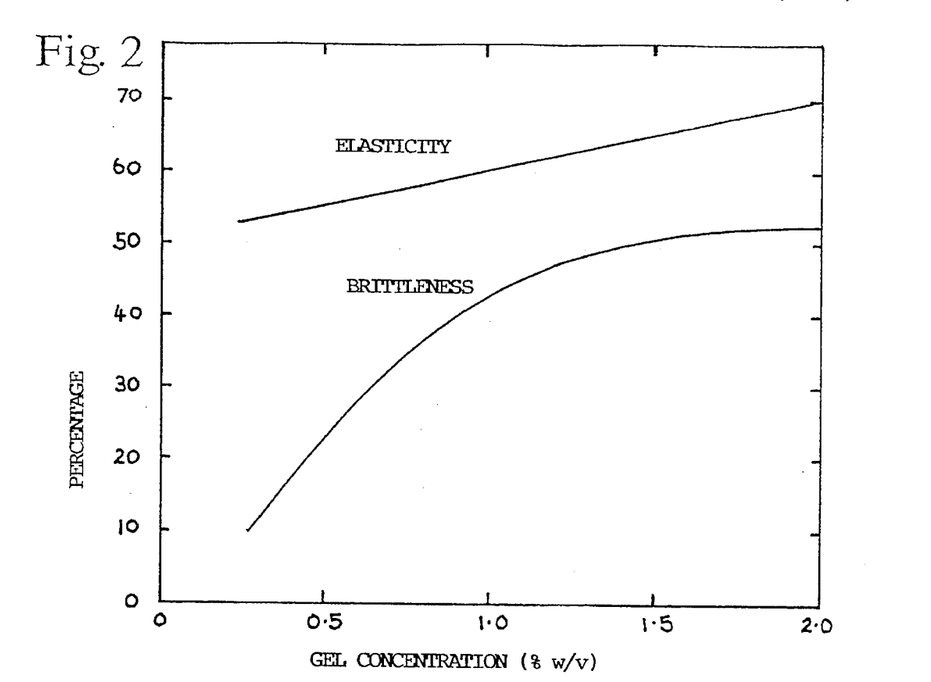
FIG. 2 illustrates the variation of elasticity and brittleness with polysaccharide concentration of a gel according to the present invention.
Figure 3:
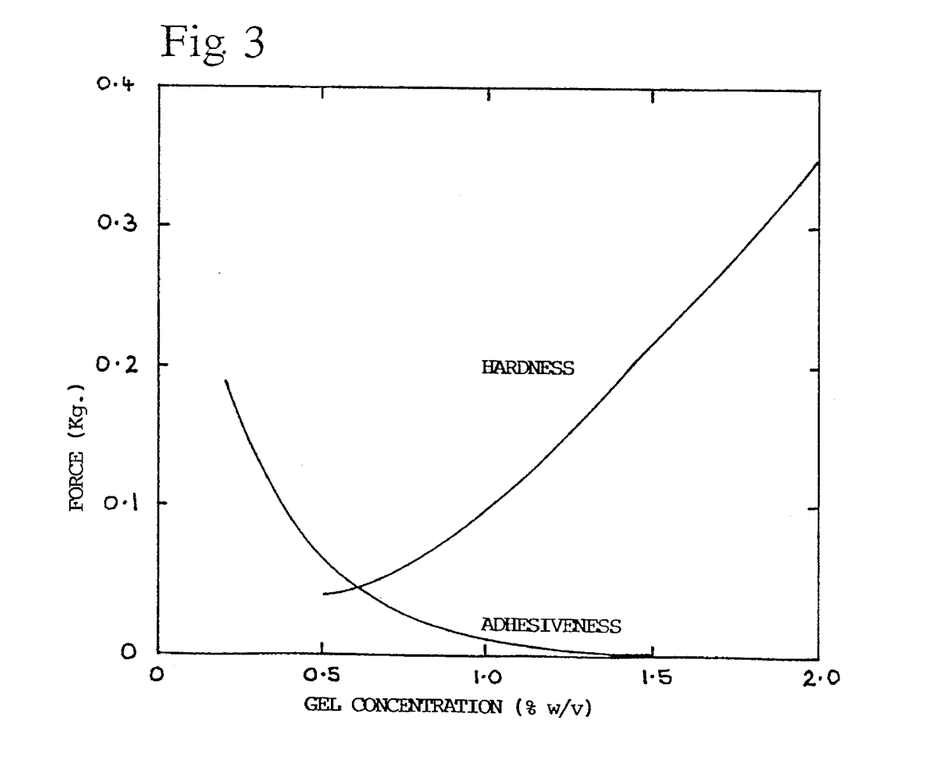
FIG. 3 illustrates the variation of hardness and adhesiveness with polysaccharide concentration of a gel according to the present invention.

FIGS. 2 and 3 respectively show the variation of elasticity and brittleness, hardness and adhesiveness with polysaccharide concentration of the gel (w/v).

EXAMPLE 2

Co-Gelling of Corn Bran and Wheat Bran Extracts
1. An extract of corn bran was prepared as in steps 1–4 of Example 1.
2. Wheat bran was macerated in hot water (70°0 C.) and hot water soluble gums and starches removed by centrifugation at 2500 rpm for 15 minutes discarding the supernatants.
3. The pellet of insoluble material was resuspended in hot water (80° C.) and further centrifuged to remove soluble matter. This procedure was repeated until no more soluble matter was removed.
4. The remaining insoluble matter was suspended to 10% w/v in 2% KOH and stirred gently at 65°–80° C. for 2–3 hours, after which insoluble material was removed by centrifugation at 2500 rpm for 20 minutes.

5. The supernatant was neutralised with acid (hydrochloric or citric) and dialysed against running water for 2 days.

6. The extract obtained from steps 1–5 and the corn bran extract obtained from steps 1–4 of Example 1 were mixed so as to give a solution containing wheat bran extract at 2.0% w/v and corn bran extract at 0.5% w/v. To 100 ml of this mixture as added 1 ml of 100 micrograms/ml horseradish peroxidase with mixing, followed by 0.5 ml hydrogen peroxide at 40 micrograms $H_2O_2$/ml. After mixing the solution was left to set for 5–15 minutes at room temperature, for 1–2 minutes at 40° C. or for less than one minute at 50° C.

In contrast, neither the 2.0% wheat bran nor the 0.5% corn bran extracts described above would form a firm gel when used alone.

EXAMPLE 3

Purification of Corn Bran Extract

An extract of corn bran prepared as in steps 1–4 of Example 1 was purified as follows:

1. Neutralisation

The extract was neutralised with hydrochloric acid to pH 6–6.5 and diluted to about 1.5% dry matter with water.

2. Salt Removal (Optional)

The extract was desalted by dialysis against running water for 3 days. Alternatively this step may involve tangential flow ultrafiltration.

3. Separation

The extract was then passed through a column containing activated carbon at a rate of 2–4 bed volumes per hour until the capacity of the column was exhausted. An eluate which was substantially free of mono and oligosaccharides, free ferulic and diferulic acids, and other organic compounds which contribute to colour and odour, was obtained.

4. Concentration

The eluate was concentrated by precipitation with ammonium sulphate (other precipitating reagents such as ethanol, IMS propan-2-ol or methanol could have been used). Alternatively the concentration could have been carried out by drying (spray or vacuum rotary drying) and redissolving of the eluate.

5. Precipitation

The redissolved precipitate produced in stage 4 was subjected to alcohol precipitation by adding 2.8 volume of alcohol.

6. Peroxide Treatment

The redissolved precipitate was added to water to produce a gelling medium of hemicellulosic concentration between 0.5 and 3.0% w/v. 30–100 micromoles of peroxide per gram of the polysaccharide and 100–200 microgram of peroxidase enzyme were added to the medium.

The above purification process could similarly be applied to wheatbran extract.

EXAMPLE 4

The presence of diferulate cross-links in a gel material according to the present invention was investigated spectrophotometrically.

Figure 4A:
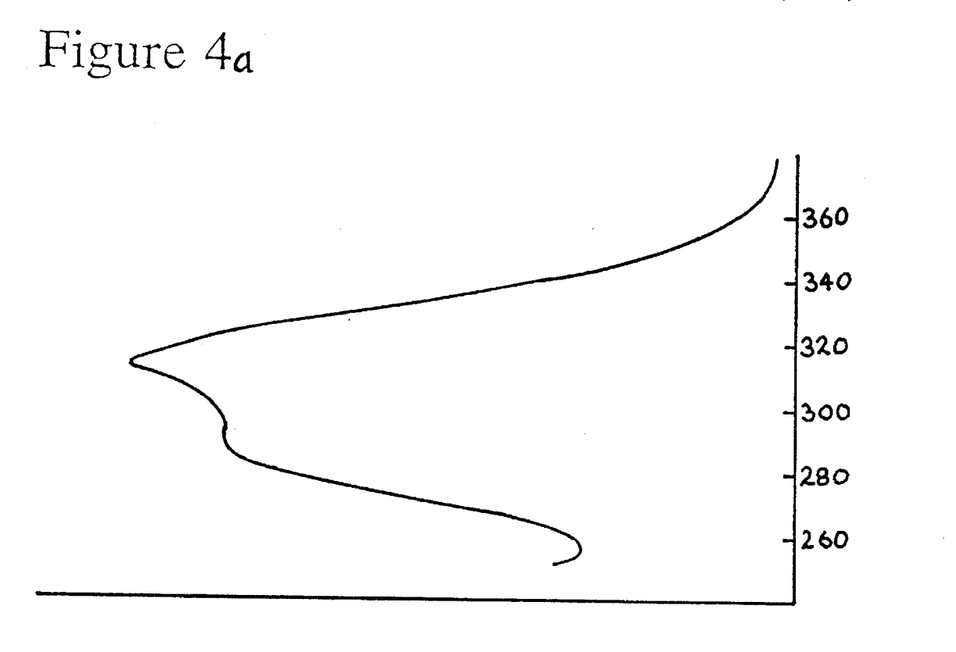
FIGS. 4a and 4b illustrate the UV spectra of (i) a ferulic acid solution (FIG. 4a), and (ii) a gel according to the present invention (FIG. 4b)
Figure 4B:
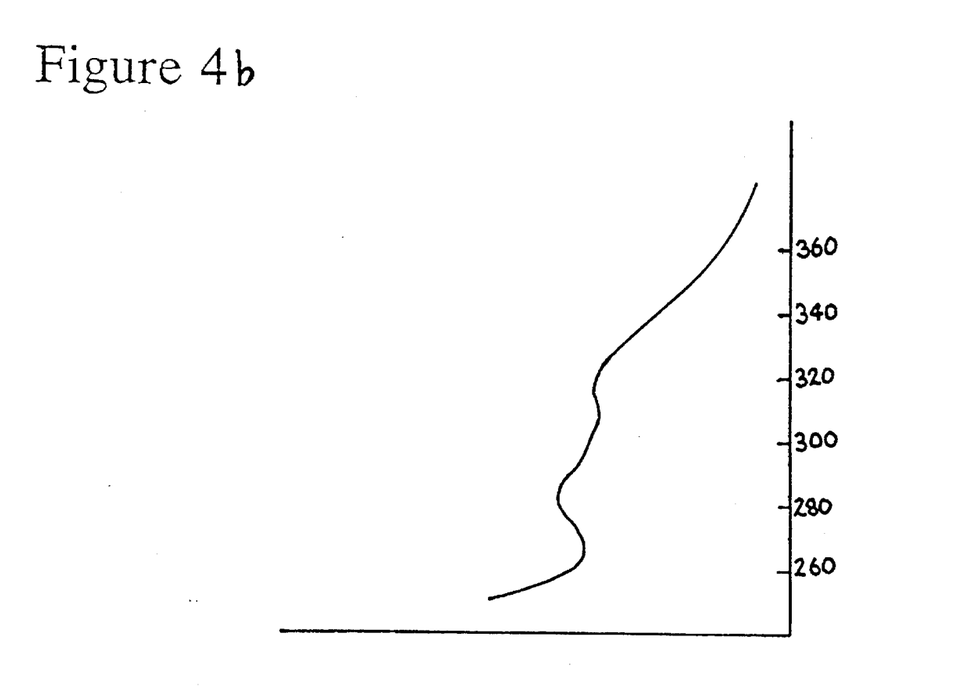

It can be seen with reference to the ultra-violet spectrum shown in FIG. 4a that a characteristic absorbance peak was obtained for a 50 μM ferulic acid solution at an excitation wavelength of about 320 nm. (Ferulic acid being known to have an absorbance peak at 320 nm, coefficient of extinction=15,100 for this peak, while diferulate shows little absorbance at this wavelength). Conversely, with reference to FIG. 4b, no such characteristic absorbance peak was obtained at 320 nm for a gel according to the present invention, thus confirming the absence of ferulic acid residues from the gel.

It was found to be possible to investigate the extent of the diferulate cross-linking in the gel by correlating the UV absorbance of the gel against an ungelled polysaccharide having ferulic acid residues.

Figure 5:
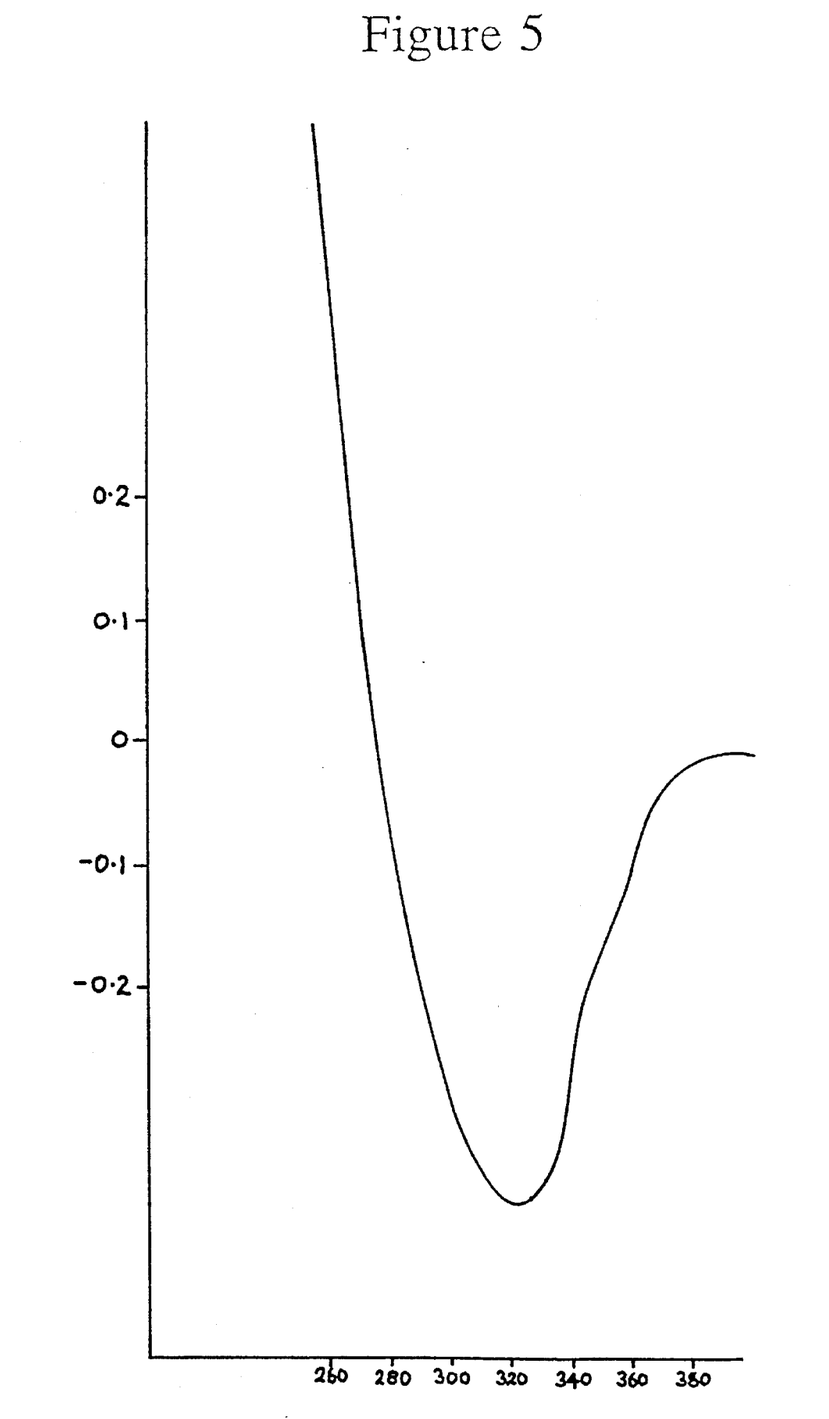
FIG. 5 is a UV reference spectra from which the extent of diferulate cross-linking in a gel according to the present invention can be estimated.

The correlation was achieved by measuring the uv absorbance of the gel at 320 nm, against the absorbance of the ungelled polysaccharide at the same wavelength. FIG. 5 shows the negative absorbance peak obtained, the extent of diferulate cross-linking was estimated from the negative peak.

EXAMPLE 5

The diferulate cross-linking was further investigated by infra-red spectrophotometry.

Substituted aromatic acids have many characteristic bands of absorbance between wave numbers 1480 and 1700 $cm^{-1}$ and between wave numbers 1000 and 1250 $cm^{-1}$.

The appearance of additional peaks of absorbance at about 1550–1600 $cm^{-1}$ and at around 1100–1160 $cm^{-1}$ is characteristic of substituted biphenyl groups and is indicative of the formation of diferulate.

Figure 6A:
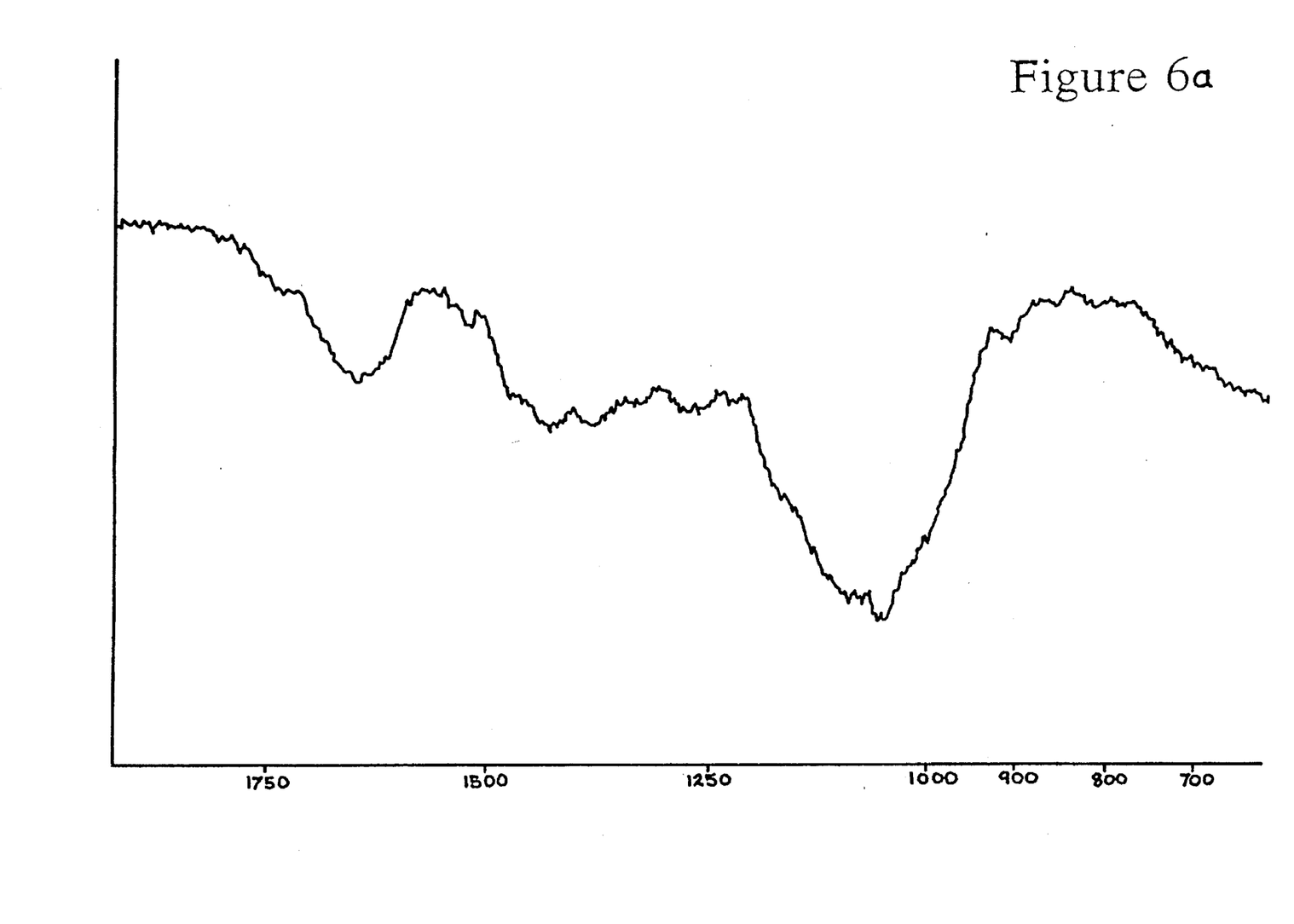
FIGS. 6a and 6b illustrate IR spectra of (i) an ungelled polysaccharide (FIG. 6a), and (ii) a gel according to the present invention (FIG. 6b).
Figure 6B:
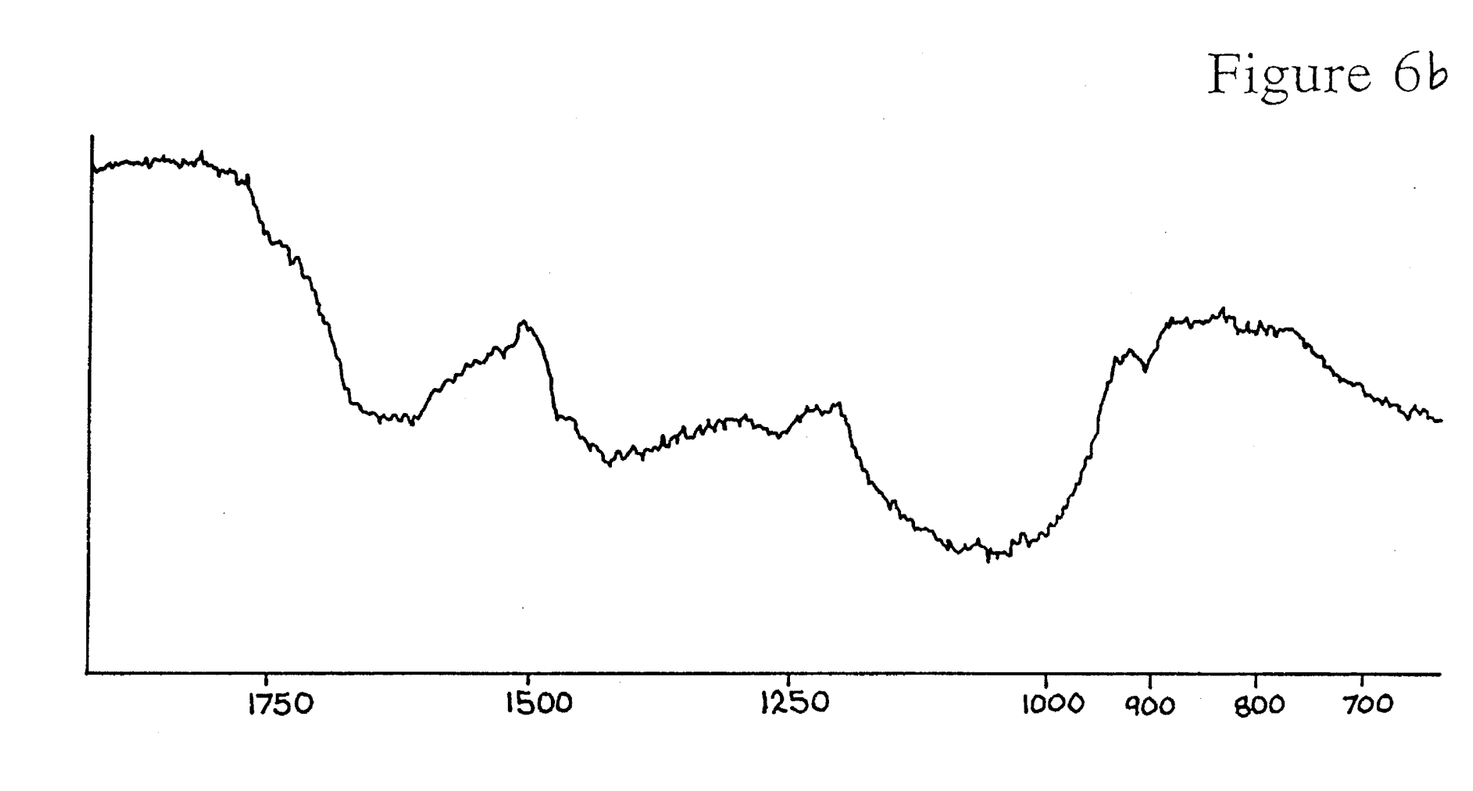

It can be seen from comparisons of FIG. 6a (an infra-red spectrum of an ungelled polysaccharide) and FIG. 6b (an infra-red spectrum of a gel according to the present invention) that there are additional absorbance peaks in the wavelength region 1550 to 1600 $cm^{-1}$, and 1100–1160 $cm^{-1}$. The additional peaks were attributed to the presence of diferulate cross-links as discussed above.

We claim:

1. A gel material obtained from a starch-free water-soluble hemicellulosic material derived from American corn bran *Zea mays*, which gel material is free of glucans and pectins and comprises a polysaccharide network which comprises:
   (i) a matrix of polysaccharide chains; and
   (ii) a multiplicity of ferulate bridges cross-linking said polysaccharide chains at regular intervals along said polysaccharide chains, said gel material having infrared absorbances in the wavelength range of 1550–1600 $cm^{-1}$ and in the wavelength range of 1100–1160 $cm^{-1}$.

2. A gel material according to claim 1, wherein said polysaccharide chains contain about 10% to about 20% arabinoxylan and/or glucuronoarabinoxylan moieties.

3. A gel material according to claim 1, having a molecular weight in the range of 80 to 600 kdaltons.

4. A gel material according to claim 1, which contains one or more metal cations selected from the group consisting of $Ca^{2+}$, $Cu^{2+}$, $Zn^{2+}$, $Fe^{3+}$ and $Al^{3+}$.

5. A method of producing a gel material, which method comprises:
   (a) providing a starch-free starting medium derived from American corn bran *Zea mays* and comprising a water soluble hemicellulosic material which is free of glucans;
   (b) extracting said hemicellulosic material with a non-acidic aqueous reagent; and
   (c) reacting the extracted hemicellulosic material with an oxidizing system comprising a peroxide, together with an oxygenase, so as to produce a gel material which comprises a matrix of polysaccharide chains, and a multiplicity of ferulate bridges cross-linking said polysaccharide chains at regular intervals along said polysaccharide chains.

6. A method according to claim 5, wherein the starting medium in step (a) is in a ground form.

7. A method according to claim 6, wherein the ground starting medium is enzyme treated, air classified or sieved to remove starch prior to step (b).

8. A method according to claim 7, wherein the enzyme treatment comprises treatment with an enzyme selected from the group consisting of alpha-amylase, beta-amylase or a mixture thereof.

9. A method according to claim 5, wherein the glucans have been removed from the starting medium by enzyme digestion with a carbohydrase enzyme.

10. A method according to claim 5, wherein the non-acidic aqueous reagent of step (b) is an alkali selected from the group consisting of NaOH and KOH.

11. A method according to claim 10, wherein the alkali is used in an amount of 0.1% to 10% by weight of said aqueous reagent for a time of from 20 minutes to 5 hours.

12. A method according to claim 11, wherein the alkali is used in an amount of 0.5 to 2.5% by weight of said aqueous reagent for about 2 hours.

13. A method according to claim 10, wherein the extraction of step (b) is carried out at a temperature of from 30° C. to 100° C.

14. A method according to claim 5, wherein the extraction of step (b) is carried out with water at a temperature of 50° C. to 80° C. for 0.5 to 2 hours.

15. A method according to claim 5, which comprises treatment with an acid and precipitation with an alcohol following step (b) and prior to step (c).

16. A method according to claim 15, wherein the acid is acetic acid.

17. A method according to claim 5, wherein the resulting gel material is dried.

18. A method according to claim 15, wherein the alcohol is ethanol.

19. A method according to claim 18, wherein the alcohol is added in an amount of from 1.5 to 3.5 volumes.

20. A method according to claim 5, wherein the hemicellulosic material which is extracted in step (b) is then passed through an activated carbon column prior to step (c) to produce a purified hemicellulosic material.

21. A method according to claim 20, wherein said purified hemicellulosic material is precipitated with ammonium sulfate, methanol, ethanol or iso-propanol prior to step (c) to produce a concentrated, purified hemicellulosic material.

22. A method according to claim 21, wherein the salt content of said concentrated, purified hemicellulosic material is lowered by dialysis or tangential flow ultrafiltration prior to step (c).

23. A method according to claim 5, wherein the oxygenase comprises a peroxidase.

24. A method according to claim 23, wherein the peroxidase comprises horseradish peroxidase.

25. A method according to claim 5, wherein the peroxide comprises hydrogen peroxide.

26. A method according to claim 5, which further comprises the addition of polyvalent metal cations to said starting medium of step (a) or to said extracted hemicellulosic material of step (b) prior to step (c).

27. A method according to claim 26, wherein said polyvalent metal cations are selected from the group consisting of $Ca^{2+}$, $Cu^{2+}$, $Zn^{2+}$, $Fe^{3+}$ and $Al^{3+}$.

28. A gel material produced by the method of claim 5.

29. A wound dressing having a surface for contact with a wound, said surface comprising a gel material according to claim 1.

30. A wound dressing according to claim 29, which consists essentially of said gel material.

31. A method for treatment of wounds, which comprises applying thereto the gel material of claim 1.

* * * * *